United States Patent
Lim et al.

(12) 
(10) Patent No.: US 6,192,277 B1
(45) Date of Patent: Feb. 20, 2001

(54) IMPLANTABLE DEVICE WITH BEVEL GEAR ACTUATION FOR LEAD RETENTION AND ACTUATION

(75) Inventors: Wisit Lim, Palmdale; Buehl E. Truex, Glendora, both of CA (US)

(73) Assignee: Pacesetter, Inc., Sylmar, CA (US)

( * ) Notice: Under 35 U.S.C. 154(b), the term of this patent shall be extended for 0 days.

(21) Appl. No.: 09/348,102

(22) Filed: Jul. 6, 1999

(51) Int. Cl.[7] .................................................. A61N 1/375
(52) U.S. Cl. ............................................................ 607/37
(58) Field of Search .................................. 439/247, 248, 439/253, 254, 255, 256, 257, 660, 661, 662, 663, 784, 810, 814, 909; 607/37

(56) References Cited

U.S. PATENT DOCUMENTS

| | | | |
|---|---|---|---|
| 3,649,367 | 3/1972 | Purdy ..................................... | 136/202 |
| 3,926,198 | 12/1975 | Kolenik .......................... | 128/419 PG |
| 4,010,759 | 3/1977 | Boer .................................. | 128/419 P |
| 4,010,760 | 3/1977 | Kraska et al. .................. | 128/419 PS |
| 4,057,068 | 11/1977 | Comben ........................... | 128/419 P |
| 4,254,775 | 3/1981 | Langer ............................. | 128/419 D |
| 4,471,783 | 9/1984 | Buffet .............................. | 128/419 PS |
| 4,934,366 | 6/1990 | Truex et al. ....................... | 128/419 P |
| 5,055,109 | 10/1991 | Gould et al. ............................ | 604/95 |
| 5,235,742 | 8/1993 | Szyszkowski ............................ | 29/856 |
| 5,352,197 | 10/1994 | Hammersmark et al. ............. | 604/95 |
| 5,370,663 | 12/1994 | Lin ............................................. | 607/5 |
| 5,370,669 | 12/1994 | Daglow et al. .......................... | 607/36 |
| 5,431,695 | 7/1995 | Wiklund et al. ......................... | 607/36 |
| 5,439,482 | 8/1995 | Adams et al. ............................. | 607/5 |
| 5,456,698 | 10/1995 | Byland et al. .......................... | 607/36 |
| 5,509,928 | 4/1996 | Acken ...................................... | 607/37 |
| 5,662,692 | 9/1997 | Paspa et al. ............................. | 607/37 |
| 5,749,911 | 5/1998 | Westlund ................................. | 607/36 |
| 5,876,424 | 3/1999 | O'Phelan et al. ....................... | 607/36 |

*Primary Examiner*—Scott M. Getzow

(57) ABSTRACT

A connector system for use with a sealed implantable medical device having at least one lead receiving channel for slidably receiving a connecting end of an electrical lead comprises a support member fixed to the medical device having a threaded bore generally parallel to and spaced from the lead receiving channel, an annular seal member mounted on the support member at the open end of the lead receiving channel and coaxial and aligned therewith, and a plunger adapted for attachment to the medical device and having an inlet bore for reception of the electrical lead and an annular flange coaxial with the inlet bore. When positioned for attachment to the medical device, the annular flange is coaxial with the lead receiving channel and aligned and engageable with its associated annular seal member. A driver bevel gear is mounted on the plunger for rotation about a driver axis extending transverse of the inlet bore and a driven bevel gear is mounted on the plunger for rotation about a driven axis extending perpendicular to the driver axis and meshingly engaged with the driver bevel gear. The driven bevel gear includes an integral threaded stud coaxial therewith threadedly engaged with the threaded bore of the support member whereby rotation of the driver bevel gear in one direction effects rotation of the driven bevel gear and of the threaded stud and draws the plunger from a withdrawn position to an attached position with the annular flanges sealingly engaged with their respective annular seals.

18 Claims, 7 Drawing Sheets

IMPLANTABLE DEVICE WITH BEVEL GEAR ACTUATION FOR LEAD RETENTION AND ACTUATION

FIELD OF THE INVENTION

The present invention relates to an electrical connector used with an implantable medical device such as a pacemaker for connecting an implantable electrical lead to the electrical circuits contained within a hermetically sealed housing thereof. More particularly, the present invention relates to a connector for use with such a sealed implantable medical device that combines the connector function with the feedthrough function and that eliminates the need for the cast or other preformed epoxy connector which has previously been employed.

BACKGROUND OF THE INVENTION

While the present invention will be described in a specific manner as being applicable to a pacemaker, it will be understood that the invention is applicable to any other type of implantable medical device intended to stimulate body tissue.

Modern pacemakers monitor the activity of a heart and provide a stimulation pulse in the absence of normal heart activity. Advantageously, such devices are relatively small, light-weight and implantable. In order to sense and stimulate the heart, however, such pacemakers must be used with a pacemaker lead, an electrical conductor that carries electrical signals between the heart and the pacemaker. Advantageously, the pacemaker lead can be inserted into the heart transvenously through a relatively simple and well-known surgical procedure. Disadvantageously, one end of the lead (designated herein as the "connecting end") must be electrically and mechanically secured to the pacemaker in a way that provides for a long-term safe and secure, yet detachable connection. Those skilled in the pacemaker art have long sought for a simple, yet reliable and safe, technique for making this detachable electrical and mechanical connection between the pacemaker device and the connecting end of the pacemaker lead.

In order to appreciate the advantages of the present invention, it will help first to have a basic understanding of the manner in which the mechanical and electrical connection functions are carried out in prior art pacemakers. The main components associated with the connection function of known prior art pacemakers are shown in FIGS. 1 and 2. A pacemaker 10 electrically includes a battery 14 that powers electrical circuits 12. The pacemaker electrical circuits 12 and battery 14 are mechanically housed and hermetically sealed in a suitable housing 16. Typically, this housing or case 16 is shaped to include a flat side or platform 20 to which a suitable epoxy connector 22 can be bonded. At least one feedthrough terminal, 18, in electrical contact with the electrical circuits 12, passes through the case or housing 16 and protrudes out from the platform 20. This feedthrough terminal 18 is electrically isolated from the case 16. A platinum wire 24, or other suitable conductive element, connects the terminal 18 to a conductive connector block 26 that is fitted within the connector 22. A pacemaker lead 28, having a proximal electrode 30, connects to the pacemaker electrical circuits by inserting the proximal electrode 30 into a receiving channel 31 of the connector 22 until the electrode 30 is in contact with the connector block 24. A set screw 32 is then securely tightened using a torque wrench 34 to firmly hold the electrode 30 in both mechanical and electrical connection with the connector block 26. A septum, not shown but having the construction generally described in commonly assigned U.S. Pat. No. 5,509,928 issued Apr. 23, 1996 to Acken, is typically placed over the set screw 32 in order to prevent body fluids from seeping through the set screw hole. Further, sealing ribs or ridges 36 on the connecting end of the pacemaker lead are designed to tightly engage the inside edges of the receiving channel 31 in order to prevent any body fluids from entering into the receiving channel 31 once the connecting end of the lead has been pushed into the connector 22.

While the descriptions presented in the prior art vary greatly relative to, for example, different types of locking mechanisms for performing the mechanical connection function, or different types of arrangements for performing the electrical feedthrough function, including the use of bipolar or multiple pacemaker leads, all such systems include the use of a premolded or cast connector 22 that is bonded to a sealed pacemaker housing 16 in which the electrical circuits are located.

Typically, prior art connectors 22 are cast in place from epoxy to the platform or header 20 of the pacemaker, or a premolded connector is bonded to the platform 20 using a suitable sealing and bonding agent. Further, once the electrical connection is made from the terminal post 18 to the connector block 26, and the connector is attached to the housing, all remaining voids within the connector 22, not including the receiving channel 31 into which the proximal end of the pacemaker lead 28 is to be inserted, must be filled with a suitable filler material, such as a two-component epoxy or silicone rubber.

As is evident from the above description, placing a connector on a pacemaker housing is a very labor-intensive process involving many components. What is needed is a similar manner of lead attachment that provides the requisite mechanical and electrical connection functions using fewer components and less labor yet providing higher reliability. The present invention addresses these and other needs.

It was with knowledge of the foregoing state of the technology that the present invention has been conceived and is now reduced to practice.

SUMMARY OF THE INVENTION

The present invention provides a connector for a pacemaker, or other implantable medical device, that advantageously combines the connector function with the feedthrough function and eliminates the need for the cast epoxy connector previously used on prior art pacemakers. Eliminating the external cast epoxy connector advantageously eliminates the need for septums, set screws, and the feedthrough terminal and its associated platinum wires and connector blocks, as well as the whole time consuming casting process with its inherent propensity for cosmetic problems. Thus, in accordance with the invention, a connector system is provided for use with a sealed implantable medical device having at least one lead receiving channel for slidably receiving a connecting end of an electrical lead and comprises a support member fixed to the medical device having a threaded bore generally parallel to and spaced from the lead receiving channel, an annular seal member mounted on the support member at the open end of the lead receiving channel and coaxial and aligned therewith, and a plunger adapted for attachment to the medical device and having an inlet bore for reception of the electrical lead and an annular flange coaxial with the inlet bore. When positioned for attachment to the medical device, the annular flange is coaxial with the lead receiving channel and aligned and engageable with its associated annular seal member. A driver bevel gear is mounted on the plunger for rotation about a driver axis extending transverse of the inlet bore and a driven bevel gear is mounted on the plunger for rotation about a driven axis extending perpendicular to the driver axis and meshingly engaged with the driver bevel gear. The driven bevel gear includes an integral threaded stud coaxial therewith threadedly engaged with the threaded bore of the support member whereby rotation of the driver bevel gear in one direction effects rotation of the driven bevel gear and of the threaded stud and draws the plunger from a withdrawn position to an attached position with the annular flanges sealingly engaged with their respective annular seals.

It is a feature of the present invention to provide a connector system that eliminates the need for the cast epoxy type of connectors used in prior art pacemakers, and the many problems and excessive cost associated with the use of such cast connectors.

It is a further feature of the present invention to provide a pacemaker or other implantable medical device that can be made from fewer components and that provides the requisite mechanical and electrical feedthrough functions at lower cost and higher reliability than prior art connection systems.

Still a further feature of the present invention is to provide a pacemaker that can be smaller than pacemakers of the prior art that perform an equivalent function.

Yet a further feature of the present invention is to provide a connection system for use with an implantable medical device, such as a pacemaker, that firmly yet detachably locks and seals the connecting end of a pacemaker lead thereto but that does not require the use of set screws, septums or equivalent mechanical securing and sealing devices.

A still further feature of the present invention is to provide a connection system for use with implantable medical devices that is compatible with existing pacemaker leads, whereby a medical device having the connection system of the present invention may replace a prior art system and still utilize an existing implantable or implanted pacemaker lead that was used with the prior art system.

Yet another further feature of the present invention is to provide a connection system for use with implantable medical devices which utilizes meshingly engaged bevel gears to easily and effectively impart the locking and sealing functions required.

Still another feature of the present invention is to provide a connection system for use with implantable medical devices which utilizes a support member fixed to the medical device having a threaded bore generally parallel to and spaced from the lead receiving channel, an annular seal member mounted on the support member at the open end of the lead receiving channel and coaxial and aligned therewith, a plunger adapted for attachment to the medical device and having an inlet bore for reception therethrough of the pacemaker lead and an annular flange coaxial with the inlet bore and, when positioned for attachment to the medical device, the annular flange being coaxial with the pacemaker lead receiving channel and aligned and engageable with the annular seal member, a driver bevel gear mounted on the plunger for rotation about a driver axis extending transverse of the inlet bore, and a driven bevel gear mounted on the plunger for rotation about a driven axis extending perpendicular to the driver axis and meshingly engaged with the driver bevel gear, the driven bevel gear including an integral threaded stud coaxial therewith threadedly engaged with the threaded bore of the support member, whereby rotation of the driver bevel gear in one direction effects rotation of the driven bevel gear and of the threaded stud and draws the plunger from a withdrawn position to an attached position with the annular flange sealingly engaged with the annular seal member.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

DETAILED DESCRIPTION OF THE PREFERRED EMBODIMENTS

Figure 1:
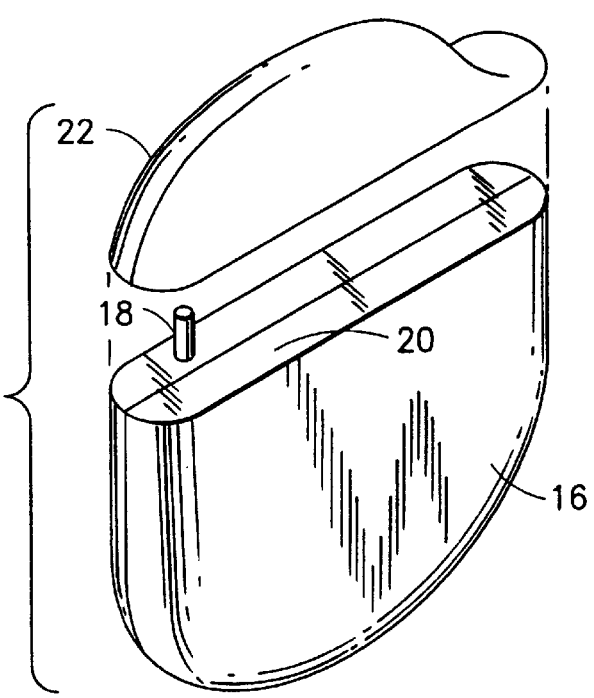
FIG. 1 is an exploded perspective view of a known pacemaker, illustrating a sealed pacemaker housing and its associated cast epoxy connector top.
Figure 2:
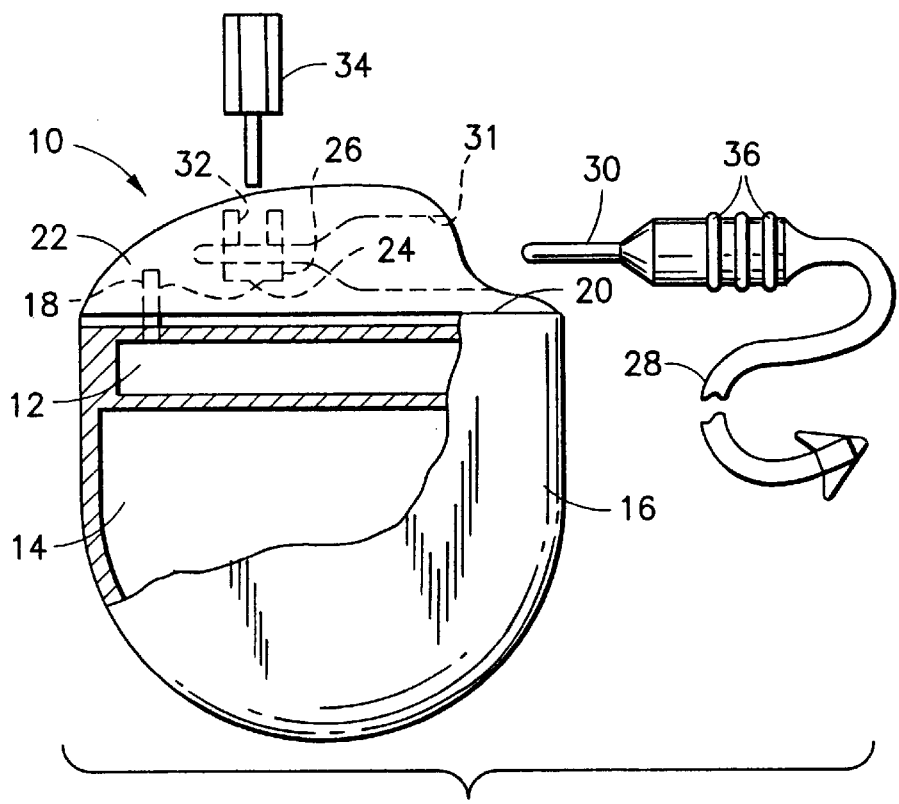
FIG. 2 is a side elevation view, partially cut away and in section, illustrating the assembled relationship between the pacemaker of FIG. 1 and its associated electrical pacemaker lead.
Figure 3:
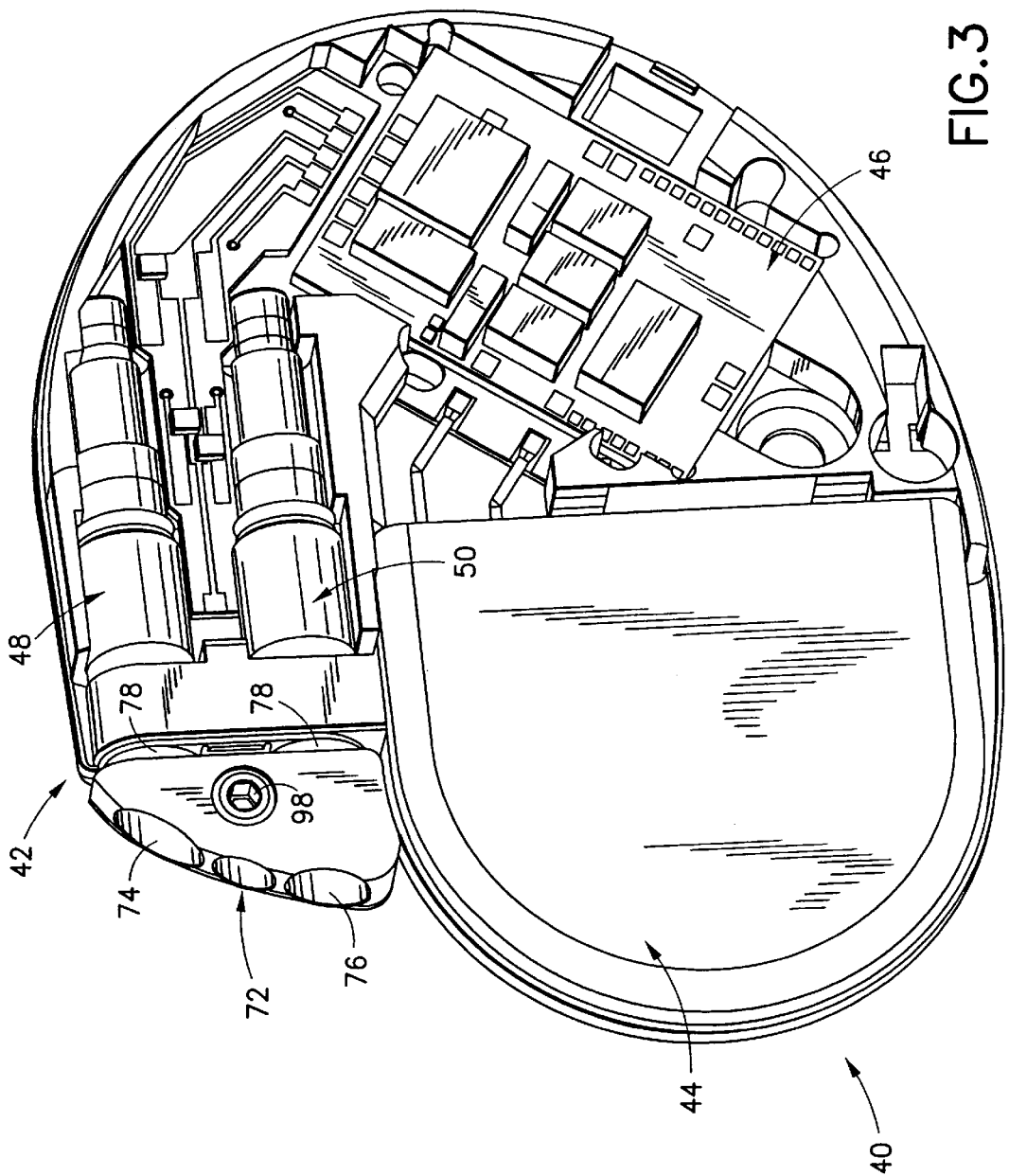
FIG. 3 is a perspective view of a pacemaker embodying the present invention, with the cover removed to illustrate the interior regions and with a plunger component in place.

Referring now to FIG. 3, there is shown a perspective view of a hermetically sealed implantable medical device in the form of a pacemaker 40 incorporating features of the present invention, namely a connector system 42. Although the present invention will be described with reference to the single embodiment shown in the drawings, it should be understood that the present invention can be embodied in many alternate forms. In addition, any suitable size, shape or type of elements or materials could be used.

Figure 6:
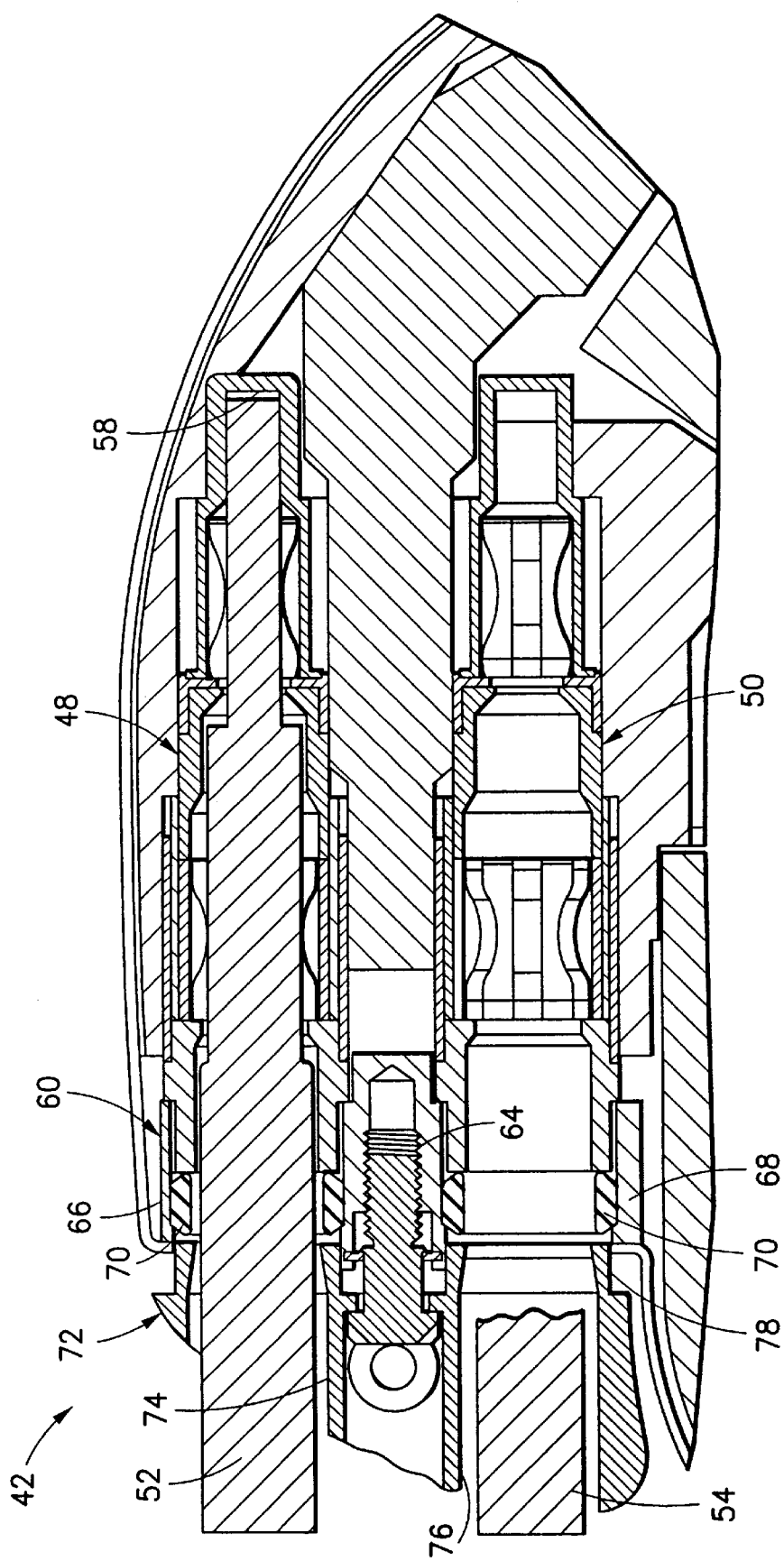
FIG. 6 is a detail cross section view, in elevation, of a portion of the pacemaker illustrated in FIG. 3, to which electrical pacemaker leads have been connected.

More specifically, the pacemaker 40 is powered by a battery 44, includes electronic circuitry 46 and, in a typical but not necessarily mandatory fashion, has at least one lead receiving channel, two channels 48, 50 being illustrated, each for slidably receiving a connecting end of an associated electrical pacemaker lead 52, 54, respectively, (FIG. 6) and defining a channel having an open end 56 for receiving the electrical pacemaker lead and a closed end 58.

A support member 60 is fixed, as by welding, to the pacemaker 40 and includes a hub 62 (FIG. 4) with a threaded bore 64 (FIG. 6) generally parallel to and spaced from the lead receiving channels 48, 50. The support member also includes a pair of integral opposed annular sleeves 66, 68 axially aligned, respectively, with the lead receiving channels 48, 50. An annular resilient seal member 70 of silicone rubber or other suitable material is mounted on the support member 60 at the open end of, and coaxial and aligned with, each of the lead receiving channels. More specifically, the annular seals are located within, and bear against, each of the sleeves 66, 68.

Figure 6A:
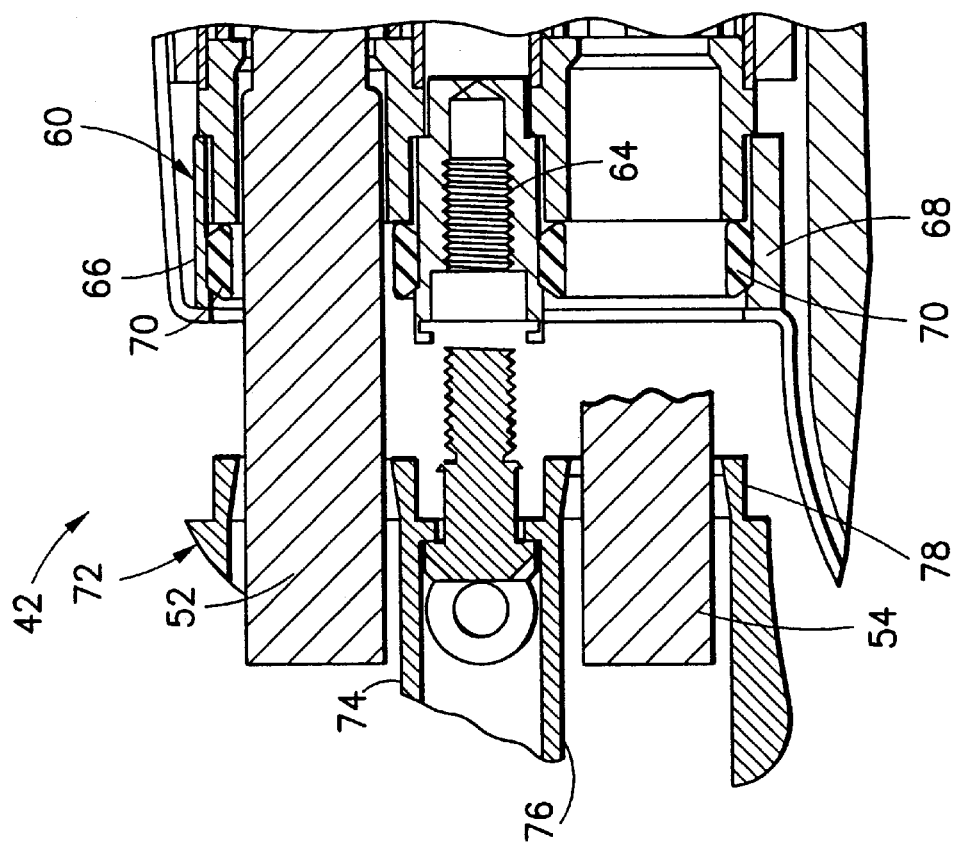
FIGS. 6A and 6B are detail cross section views of the left end portion of FIG. 6 and illustrating, respectively, an attached position and a withdrawn position of the plunger component.
Figure 6B:
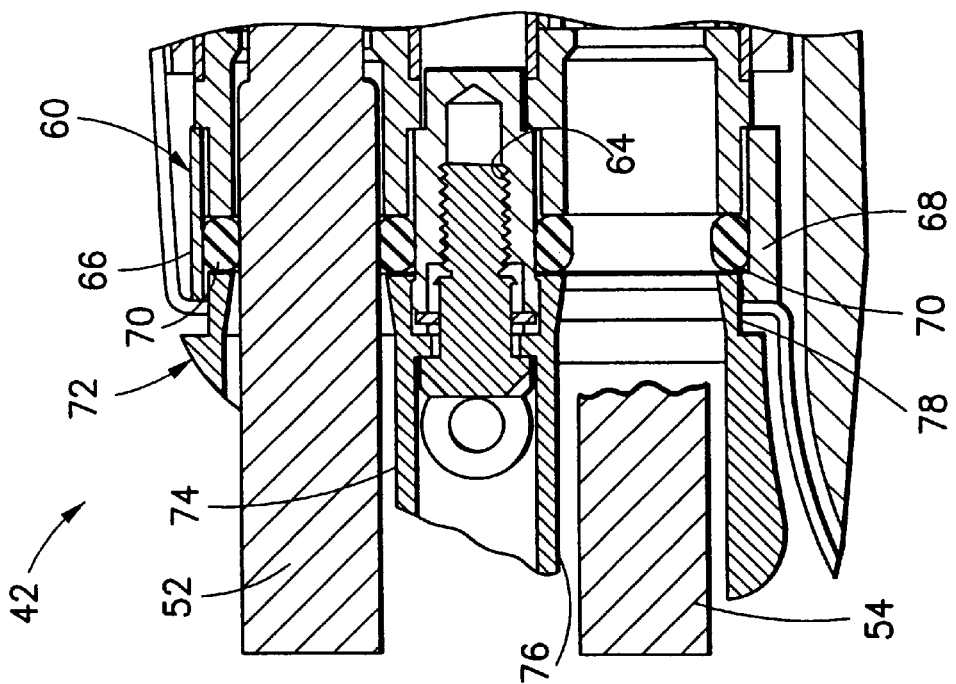
Figure 7:
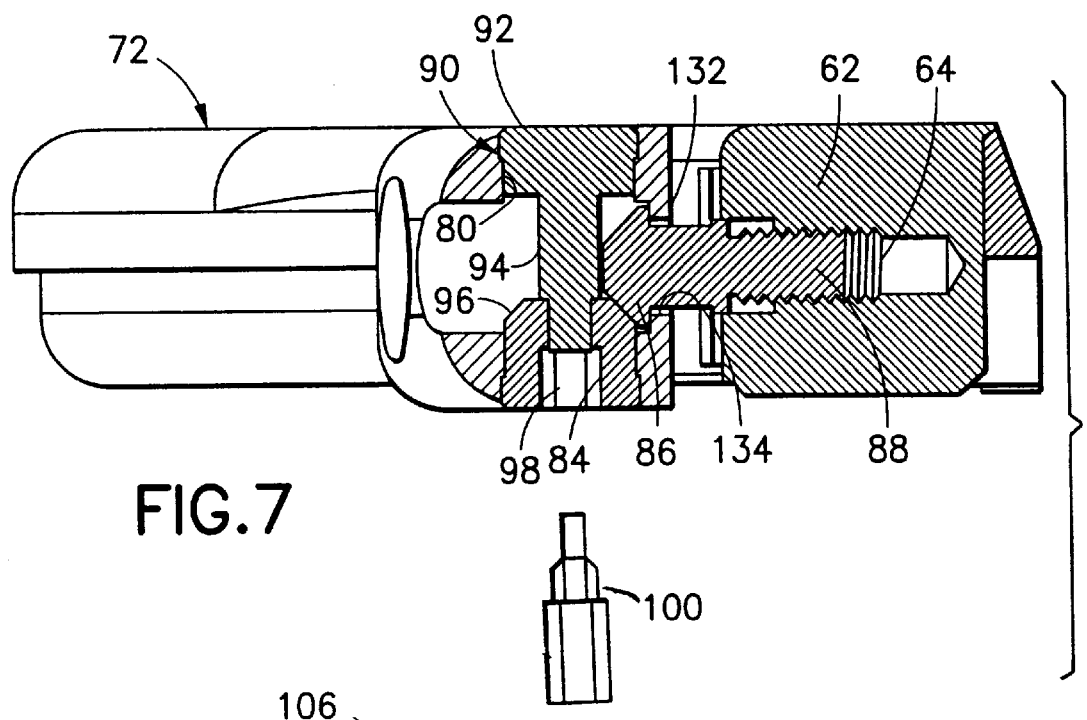
FIG. 7 is a top plan view, certain parts being cut away and shown in cross section, of components illustrated in FIGS. 6A and 6B.
Figure 8:
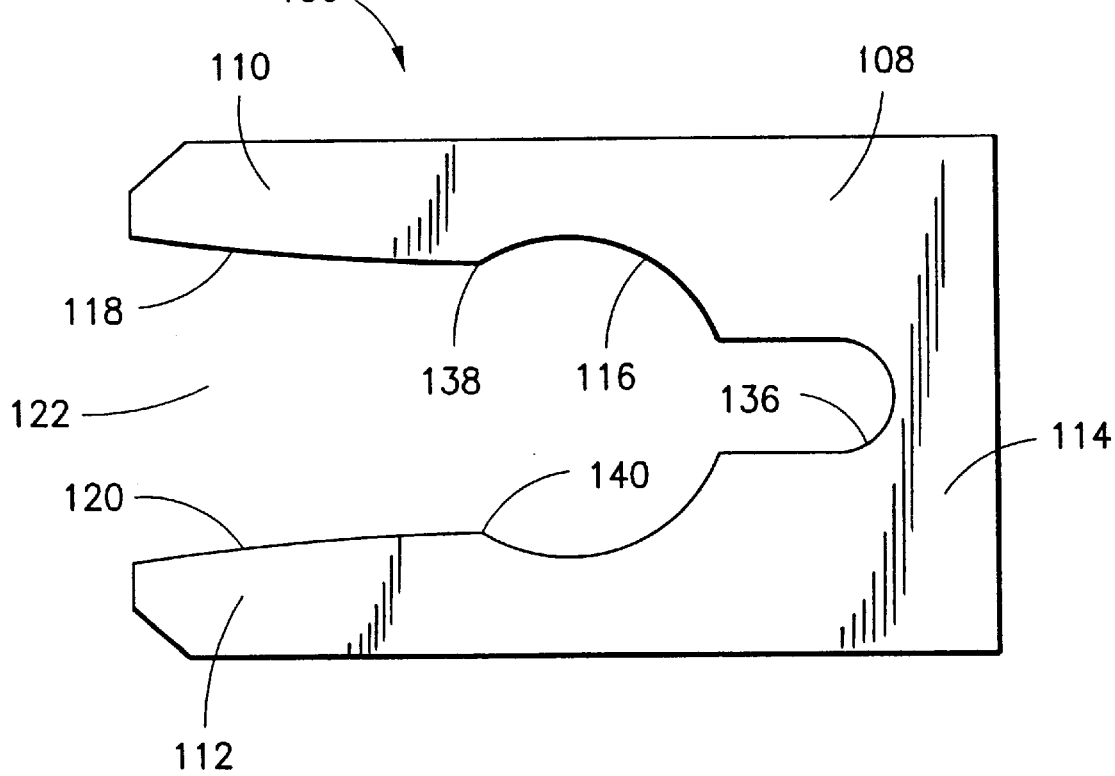
FIG. 8 is a detail elevation view of another component used with the invention.

A plunger 72 is adapted for attachment to the pacemaker 40 and has at least one inlet bore, two inlet bores 74, 76 being illustrated, for reception therethrough, respectively, of the electrical pacemaker leads 52, 54 and an annular flange 78 coaxial with each of the inlet bores. When positioned for attachment to the pacemaker 40, each of the annular flanges 78 is coaxial with a respective one of the lead receiving channels 48, 50 and aligned and engageable with an associated annular seal member 70. Additionally, each of the annular flanges 78 of the plunger is telescopingly received within an associated sleeve 66, 68 when the plunger is moved from a withdrawn position (FIG. 6B) to an attached position (FIG. 6A) with the annular flanges being sealingly engaged with their respective annular seals.

The plunger is formed with a first retainer bore 80 having an axis which is transverse of the inlet bores 74, 76 and with a second retainer bore 82 which is perpendicular to the first retainer bore. In a manner to be more fully explained, a driver bevel gear is mounted on the plunger within the retainer bore 80 for rotation about a driver axis which is coincident with the axis of the retainer bore 80. At the same time, a driven bevel gear 86 is mounted on the plunger within the retainer bore 82 for rotation about a driven axis which is coincident with the axis of the retainer bore 82. The driven bevel gear 86 is meshingly engaged with the driver bevel gear 84 and includes an integral threaded stud 88 coaxial therewith and threadedly engaged with the threaded bore 64 of the support member 60. With this construction, rotation of the driver bevel gear 84 in one direction effects rotation of the driven bevel gear 86 and of the threaded stud 88 and draws the plunger 72 from the withdrawn position (FIG. 6B) to the attached position (FIG. 6A) with the annular flanges 78 sealingly engaged with their respective annular seal members 70.

The connector system 42 also includes a first retainer 90 for mounting the driver bevel gear 84 within the retainer bore 80. The first retainer 90, in turn, includes a head member 92 journaled with the plunger 72 in the retainer bore 80 and an axle member 94 projecting from the head member. The driver bevel gear 84 is fixedly mounted, as by welding, on a necked-down extremity 96 of the axle member 94 spaced from the head member 92 for unitary rotation with the axle member. As with the head member 92, the driver bevel gear is journaled with the plunger in the retainer bore 80.

The driver bevel gear 84 has a hex-shaped recess 98 in a gear head 126 thereof for receiving a similarly shaped tool 100 to impart rotation thereto and, therefore, to the driven bevel gear 86.

Figure 4:
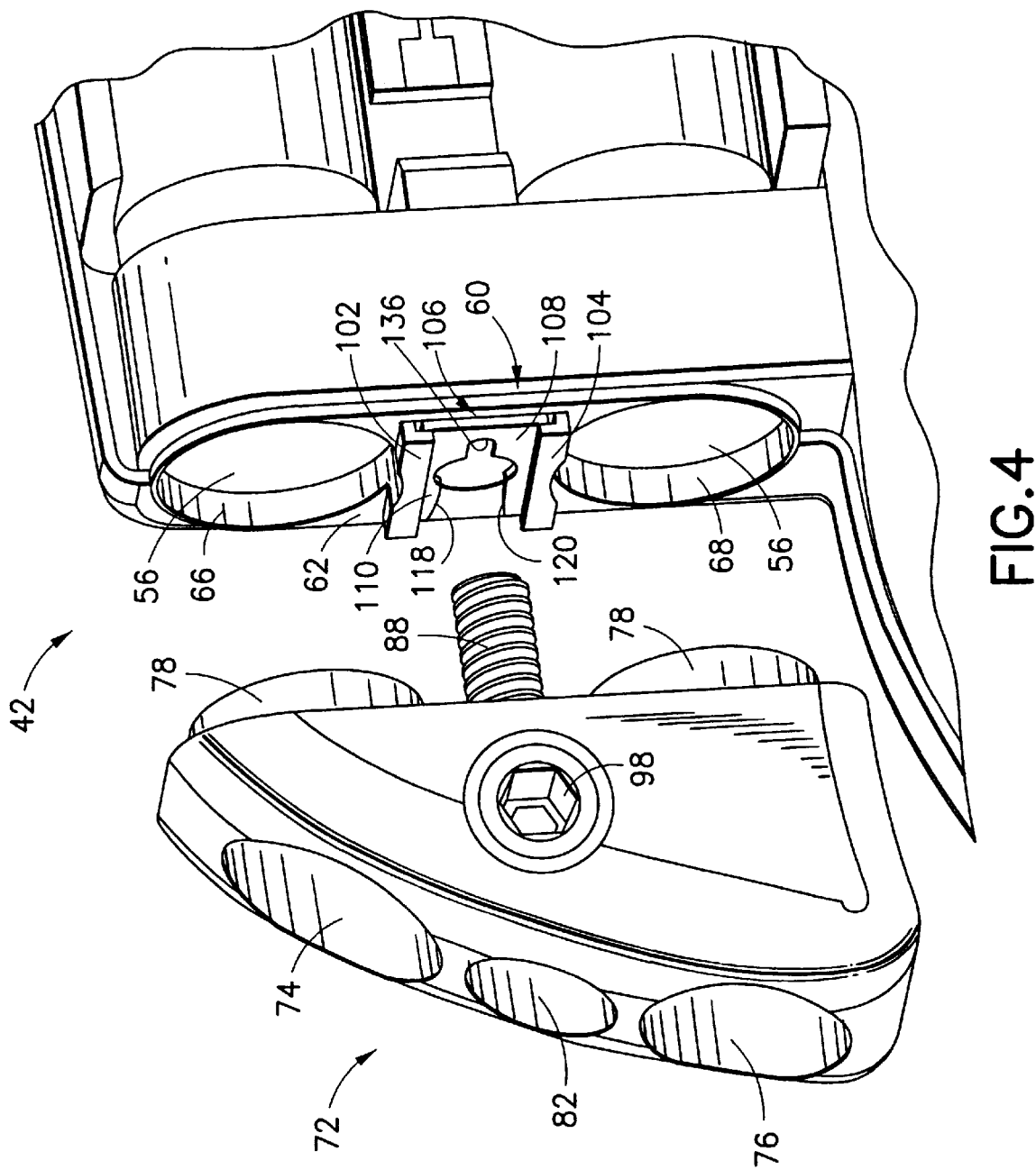
FIG. 4 is a detail perspective view of a portion of the pacemaker illustrated in FIG. 3, with the plunger component exploded therefrom.

Viewing especially FIG. 4, the support member 60 includes upper and lower parallel spaced apart linear flange members 102, 104 fixed to the hub 62 on opposite sides, respectively, of the threaded bore 64. A second retainer 106 for mounting the driven bevel gear 86 within the second retainer bore 82 includes a generally C-shaped plate 108 having a first leg 110 engaged with the upper flange member 102, a second leg 112 generally parallel to the first leg and engaged with the lower flange member 104, a bight member 114 joining the upper and lower flange members, an interior contoured surface 116 for rotatably mounting thereon the driven bevel gear 86, and opposed guide edges 118, 120 on the upper and lower flange members 102, 104, respectively, adjacent an opening 122 toward the interior contoured surface opposite the bight member 114.

Figure 5:
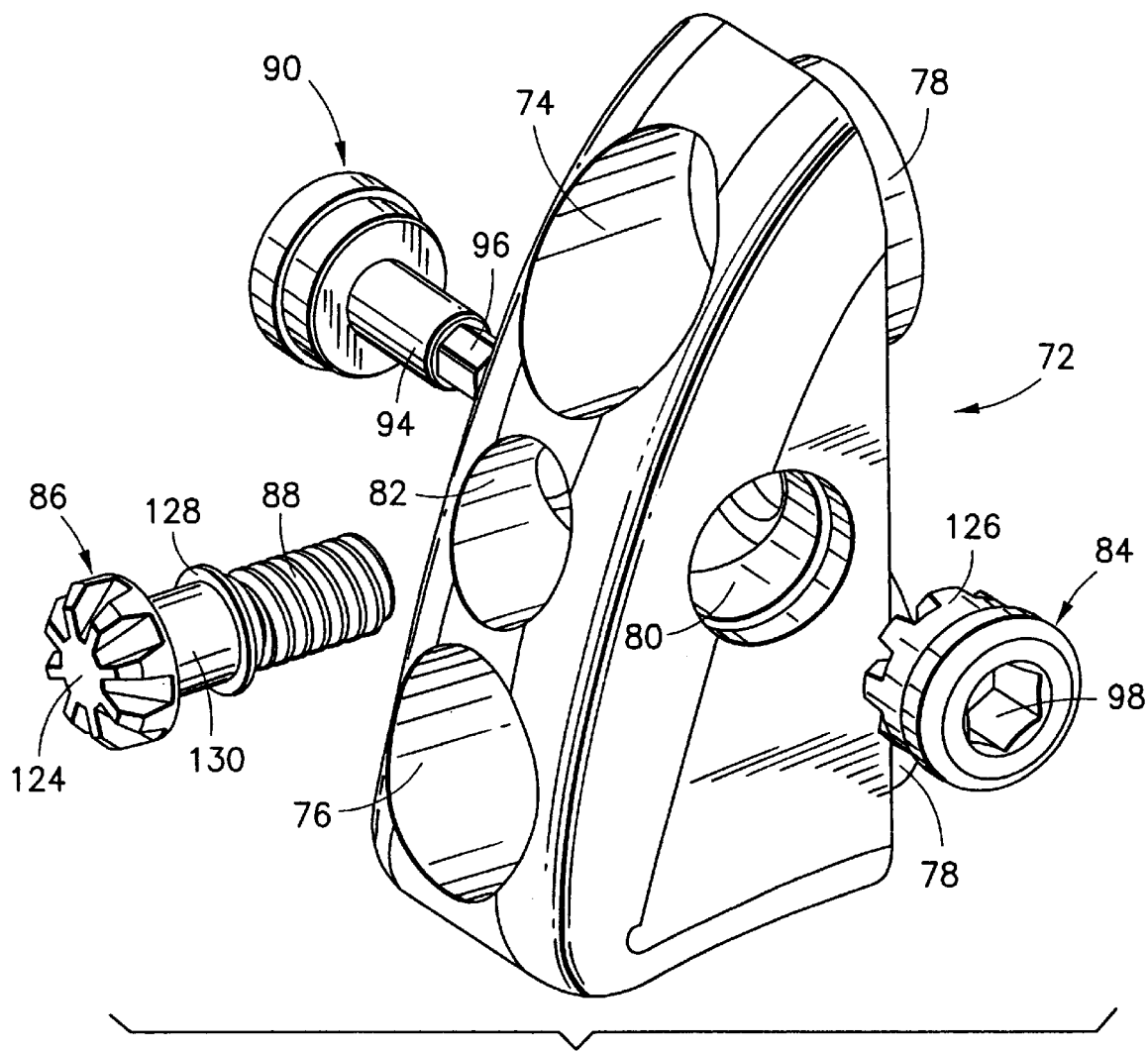
FIG. 5 is an exploded detail perspective view of the plunger component illustrated in FIG. 4 and of associated components.

The driven bevel gear 86 includes a gear head 124 for meshing engagement with a gear head 126 of the drive bevel gear 84, an annular shoulder 128 intermediate the threaded stud 88 and the gear head 124, and a cylindrical bearing surface 130 (FIG. 5) intermediate the gear head and the annular shoulder.

The plunger 72 includes an integral bearing ring 132 projecting radially into the second retainer bore 82 to a circumferential edge 134 defining an aperture for freely receiving therethrough the cylindrical bearing surface 130 of the driven bevel gear 86. During assembly of the connector system, with the gear head of the driven bevel gear 86 positioned in the second retainer bore 82, the second retainer 106 is moved laterally so that the cylindrical bearing surface 130 of the driven bevel gear is advanced into and through the opening 122 of the C-shaped plate 108 of the retainer 106 opposite the bight member 114. With the continued lateral advance of the second retainer 106, the cylindrical bearing surface of the driven bevel gear 86 is caused to move into engagement with the opposed guide edges 118, 120 on the upper and lower flange members 110, 112 until it reaches a final position rotatably engaged with the interior contoured surface 116. A cutout portion 136 in the bight 114 is suitably shaped and sized so that the legs 110, 112 yield sufficiently, first, to enable the cylindrical bearing surface 130 of the driven bevel gear to advance past opposed points 138, 140 which define the narrowest part of the opening 122, then, to capture the cylindrical bearing surface 130 for journaled engagement with the interior contoured surface 116.

In the operation of the connector system 42 of the invention, the plunger 42 is positioned initially so that the inlet bores 74, 76 are generally aligned with their associated lead receiving channels 48, 50. The electrical leads 52, 54 are then inserted through the inlet bores, through the sleeves 66, 68, and deep into the lead receiving channels. Thereupon, the tool 100 is inserted into the recess 98 of the driver gear 84 and with the resultant rotation of the driver bevel gear 84 in the appropriate direction to effect rotation of the driven bevel gear 86, the gear head 124 of the driven bevel gear engages the bearing ring 132 and the threaded stud 88 advances in threaded engagement with the threaded bore 64 of the support member 60. By so doing, the plunger 72 is drawn from the withdrawn position to the attached position with the annular flanges 78 sealingly engaged with their associated annular seal members 70. Simultaneously, the seal members are caused to expand radially inwardly to firmly and sealingly engage the outer peripheral surface of each of the electrical leads. In this manner, the electrical leads are firmly joined mechanically and electrically to the pacemaker 40 the lead receiving channels 48, 50 are sealed against entry of undesirable fluids.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A connector system adapted for attachment to a sealed implantable medical device, the connector system having a lead receiving channel for slidably receiving a connecting end of an electrical lead and defining a channel having an open end for receiving the electrical lead and a closed end, the connector system comprising:

a support member adapted for fixation to the medical device and having a threaded bore generally parallel to and spaced from the lead receiving channel;

an annular seal member mounted on the support member at the open end of the lead receiving channel and coaxial and aligned therewith;

a plunger adapted for attachment to the medical device and having an inlet bore for reception therethrough of the electrical lead and an annular flange coaxial with the inlet bore and, when positioned for attachment to the medical device, the annular flange being coaxial with the lead receiving channel and aligned and engageable with the annular seal member;

a driver bevel gear mounted on the plunger for rotation about a driver axis extending transverse of the inlet bore;

a driven bevel gear mounted on the plunger for rotation about a driven axis extending perpendicular to the driver axis and meshingly engaged with the driver bevel gear, the driven bevel gear including an integral threaded stud coaxial therewith threadedly engaged with the threaded bore of the support member;

whereby rotation of the driver bevel gear in one direction effects rotation of the driven bevel gear and of the threaded stud and draws the plunger from a withdrawn position to an attached position with the annular flange sealingly engaged with the annular seal member.

2. The connector system, as set forth in claim 1, wherein the plunger has a first retainer bore transverse of the inlet bore and a second retainer bore perpendicular to the first retainer bore, the driver bevel gear being rotatably mounted on the plunger within the first retainer bore, the driven bevel gear being rotatably mounted on the plunger within the second retainer bore.

3. The connector system, as set forth in claim 2, including:

a first retainer for mounting the driver bevel gear within the first retainer bore; and a second retainer for mounting the driven bevel gear within the second retainer bore.

4. The connector system, as set forth in claim 1, wherein the support member includes a hub and an integral sleeve axially aligned with the lead receiving channel of the medical device, the annular seal member being received within the sleeve, the annular flange of the plunger being telescopingly received within the sleeve when the plunger is moved from the withdrawn position to the attached position with the annular flange sealingly engaged with the annular seal member.

5. The connector system, as set forth in claim 4, wherein the support member includes upper and lower parallel spaced apart linear flange members fixed to the hub on opposite sides, respectively, of the threaded bore;

wherein the second retainer includes a generally C-shaped plate having a first leg engaged with the upper flange member, a second leg generally parallel to the first leg and engaged with the lower flange member, a bight member joining the upper and lower flange members, an interior contoured surface for rotatably mounting thereon the driven bevel gear, and opposed guide edges on the upper and lower flange members, respectively, adjacent an opening toward the interior contoured surface opposite the bight member; and wherein the driven bevel gear includes:

a gear head for meshing engagement with the drive bevel gear;

an annular shoulder intermediate the threaded stud and the gear head; and a cylindrical bearing surface intermediate the gear head and the annular shoulder;

wherein the plunger includes an integral bearing ring projecting radially into the second retainer bore to a circumferential edge defining an aperture for freely receiving therethrough the cylindrical bearing surface of the driven bevel gear;

whereby, during assembly, with the gear head of the driven bevel gear positioned in the second retainer bore, the second retainer is moved laterally so that the cylindrical bearing surface of the driven bevel gear is advanced through the opening opposite the bight member and into engagement with the opposed guide edges on the upper and lower flange members and reaches a final position such that the driven bevel gear is rotatably engaged with the interior contoured surface of the second retainer; and whereby, during operation, with rotation of the driver bevel gear in the one direction to effect rotation of the driven bevel gear, the gear head of the driven bevel gear engages the bearing ring and the threaded stud advances in threaded engagement with the threaded bore of the support member, thereby drawing the plunger from the withdrawn position to the attached position with the annular flange sealingly engaged with the annular seal member.

6. The connector system, as set forth in claim 1:

wherein the support member includes a hub and an integral sleeve mounted on the lead receiving channel of the medical device;

wherein, the annular seal member is received within the sleeve; and wherein, with an electrical lead positioned in the lead receiving channel and with the annular flange of the plunger being telescopingly received within the sleeve when the plunger is moved from the withdrawn position to the attached position, the annular flange sealingly engages with the annular seal member and causes the seal member to press radially inwardly into firm sealing engagement with the electrical lead.

7. The connector system, as set forth in claim 6, wherein the seal member has an outer surface formed with a circumferential notch for improved sealing capability.

8. The connector system, as set forth in claim 1, wherein the first retainer includes a head member journaled with the plunger in the first retainer bore and an axle member projecting from the head member, said drive bevel gear mounted on the axle member spaced from the head member for unitary rotation with the axle member and journaled with the plunger in the first retainer bore.

9. The connector system, as set forth in claim 8, wherein the gear head of the driver bevel gear has a shaped recess therein for receiving a similarly shaped tool to impart rotation thereto.

10. An implantable medical device having a connector system, the connector system having at least two lead receiving channels, each for slidably receiving a connecting end of an electrical lead and defining a channel having an open end for receiving the electrical lead and a closed end, the connector system further comprising:

- a support member fixed to the medical device having a threaded bore generally parallel to and spaced from the lead receiving channels;
- an annular seal member mounted on the support member at the open end of each of the lead receiving channels and coaxial and aligned therewith;
- a plunger adapted for attachment to the medical device and having at least two inlet bores for reception therethrough, respectively, of the electrical leads and an annular flange coaxial with each of the inlet bores and, when positioned for attachment to the medical device, each of the annular flanges being coaxial with a respective one of the lead receiving channels and aligned and engageable with an associated annular seal member;
- a driver bevel gear mounted on the plunger for rotation about a driver axis extending transverse of the inlet bores; and
- a driven bevel gear mounted on the plunger for rotation about a driven axis extending perpendicular to the driver axis and meshingly engaged with the driver bevel gear, the driven bevel gear including an integral threaded stud coaxial therewith threadedly engaged with the threaded bore of the support member;
- whereby rotation of the driver bevel gear in one direction effects rotation of the driven bevel gear and of the threaded stud and draws the plunger from a withdrawn position to an attached position with the annular flanges sealingly engaged with their respective annular seals.

11. The connector system, as set forth in claim 10, wherein the plunger has a first retainer bore transverse of the inlet bore and a second retainer bore perpendicular to the first retainer bore, the driver bevel gear being rotatably mounted on the plunger within the first retainer bore, the driven bevel gear being rotatably mounted on the plunger within the second retainer bore.

12. The connector system, as set forth in claim 11, including:
- a first retainer for mounting the driver bevel gear within the first retainer bore; and
- a second retainer for mounting the driven bevel gear within the second retainer bore.

13. The connector system, as set forth in claim 12, wherein the first retainer includes a head member journaled with the plunger in the first retainer bore and an axle member projecting from the head member, said drive bevel gear mounted on the axle member spaced from the head member for unitary rotation with the axle member and journaled with the plunger in the first retainer bore.

14. The connector system, as set forth in claim 13, wherein the gear head of the driver bevel gear has a shaped recess therein for receiving a similarly shaped tool to impart rotation thereto.

15. The connector system, as set forth in claim 10, wherein the support member includes a central hub and at least two integral sleeves axially aligned, respectively, with the lead receiving channels of the medical device, the annular seals being received, respectively, within each of the sleeves, each of the annular flanges of the plunger being telescopingly received within an associated sleeve when the plunger is moved from the withdrawn position to the attached position with the annular flanges sealingly engaged with their respective annular seals.

16. The connector system, as set forth in claim 15:
- wherein the support member includes upper and lower parallel spaced apart linear flange members fixed to the hub on opposite sides, respectively, of the threaded bore;
- wherein the second retainer includes a generally C-shaped plate having a first leg engaged with the upper flange member, a second leg generally parallel to the first leg and engaged with the lower flange member, a bight member joining the upper and lower flange members, an interior contoured surface for rotatably mounting thereon the driven bevel gear, and opposed guide edges on the upper and lower flange members, respectively, adjacent an opening toward the interior contoured surface opposite the bight member; and
- wherein the driven bevel gear includes:
  - a gear head for meshing engagement with the drive bevel gear;
  - an annular shoulder intermediate the threaded stud and the gear head; and
  - a cylindrical bearing surface intermediate the gear head and the annular shoulder;
  - wherein the plunger includes an integral bearing ring projecting radially into the second retainer bore to a circumferential edge defining an aperture for freely receiving therethrough the cylindrical bearing surface of the driven bevel gear;
  - whereby, during assembly, with the gear head of the driven bevel gear positioned in the second retainer bore, the second retainer is moved laterally so that the cylindrical bearing surface of the driven bevel gear is advanced through the opening opposite the bight member and into engagement with the opposed guide edges on the upper and lower flange members and reaches a final position such that the driven bevel gear is rotatably engaged with the interior contoured surface of the second retainer; and
  - whereby, during operation, with rotation of the driver bevel gear in the one direction to effect rotation of the driven bevel gear, the gear head of the driven bevel gear engages the bearing ring and the threaded stud advances in threaded engagement with the threaded bore of the support member, thereby drawing the plunger from the withdrawn position to the attached position with the annular flanges sealingly engaged with their associated annular seal members.

17. The connector system, as set forth in claim 10:
- wherein the support member includes a hub and at least two integral sleeves for slidable reception, respectively, mounted on the lead receiving channels of the medical device;
- wherein, the annular seal member is received within the sleeve; and
- wherein, with an electrical lead positioned in each lead receiving channel and with the annular flanges of the plunger being telescopingly received within its associated sleeve when the plunger is moved from the withdrawn position to the attached position, the annular flange in each instance sealingly engages with the annular seal member and causes the seal member to press radially inwardly into firm sealing engagement with the electrical lead.

18. The connector system, as set forth in claim 17, wherein each seal member has an outer surface formed with a circumferential notch for improved sealing capability.

* * * * *